United States Patent [19]

Durham et al.

[11] Patent Number: 5,272,345

[45] Date of Patent: * Dec. 21, 1993

[54] CALIBRATION METHOD AND APPARATUS FOR MEASURING THE CONCENTRATION OF COMPONENTS IN A FLUID

[75] Inventors: Michael D. Durham, Castle Rock; Francis J. Sagan, Lakewood; Mark R. Burkhardt, Denver, all of Colo.

[73] Assignee: ADA Technologies, Inc., Englewood, Colo.

[*] Notice: The portion of the term of this patent subsequent to Dec. 3, 2008 has been disclaimed.

[21] Appl. No.: 801,453

[22] Filed: Dec. 2, 1991

Related U.S. Application Data

[63] Continuation-in-part of Ser. No. 410,925, Sep. 22, 1989, Pat. No. 5,070,246.

[51] Int. Cl.$^5$ .............................................. G01J 3/32
[52] U.S. Cl. .................................. 250/373; 250/341; 356/436
[58] Field of Search ............... 250/373, 339, 340, 341, 250/351; 356/51, 436, 437

[56] References Cited

U.S. PATENT DOCUMENTS

| | | | |
|---|---|---|---|
| 2,170,435 | 8/1939 | Sweeney | 73/51 |
| 2,620,444 | 12/1952 | Heigl et al. | 250/43.5 |
| 2,690,093 | 9/1954 | Daly | 88/14 |
| 3,637,310 | 1/1972 | Naono | 356/83 |
| 3,640,625 | 2/1972 | Ibbett et al. | 356/97 |
| 3,702,736 | 11/1972 | Coggeshall | 356/96 |
| 3,732,017 | 5/1973 | Wolber | 356/201 |
| 3,880,523 | 4/1975 | Thomas | 356/79 |
| 3,887,473 | 6/1975 | Sternberg et al. | 250/345 |
| 3,893,770 | 7/1975 | Takami et al. | 356/96 |
| 3,929,398 | 12/1975 | Bates | 356/186 |
| 3,973,849 | 8/1976 | Jackson et al. | 356/97 |
| 4,054,389 | 10/1977 | Owen | 356/189 |
| 4,079,405 | 3/1978 | Ohuchi et al. | 357/30 |
| 4,084,906 | 4/1978 | Bibbero | 356/96 |
| 4,158,505 | 6/1979 | Mathisen et al. | 356/308 |
| 4,176,963 | 12/1979 | Fabinski et al. | 356/418 |
| 4,272,249 | 6/1981 | D'Antonio | 23/232 |
| 4,301,477 | 11/1981 | Takemoto et al. | 358/213 |
| 4,560,873 | 12/1985 | McGowan et al. | 250/339 |
| 4,563,585 | 1/1986 | Ward | 250/373 |
| 4,566,792 | 1/1986 | Suzuki | 356/319 |
| 4,571,074 | 2/1986 | Thevenon | 356/51 |
| 4,641,973 | 2/1987 | Nestler et al. | 356/418 |
| 4,678,917 | 7/1987 | Helms et al. | 250/373 |
| 4,723,129 | 2/1988 | Endo et al. | 346/1.1 |
| 4,740,796 | 4/1988 | Endo et al. | 346/1.1 |
| 4,746,793 | 5/1988 | Hopkins, II | 250/237 |
| 4,791,469 | 12/1988 | Ohmi et al. | 357/30 |
| 4,794,443 | 12/1988 | Tanaka et al. | 357/43 |
| 4,810,896 | 3/1989 | Tanaka et al. | 250/578 |

(List continued on next page.)

FOREIGN PATENT DOCUMENTS

| | | |
|---|---|---|
| 260858 | 3/1988 | European Pat. Off. . |
| 0277016 | 8/1988 | European Pat. Off. . |
| 2450012 | 9/1980 | France . |
| 63-076476 | 4/1988 | Japan . |

OTHER PUBLICATIONS

"Photodiode Array Detectors for LC," by Stuart A. Borman, Analystical Chemistry, 55 (8) Jul. 1983, pp. 836A-842A.
"Continuous Infrared Analysis of $N_2O$ in Combustion Products," by T. A. Montomgomery and G. S. Samuelson, JAPCA, vol. 39, No. 5, May 1989, pp. 721-726.
"Development of Low Level $NH_3$ Measuring Method," Nakabayaski et al.

Primary Examiner—Paul M. Dzierzynski
Assistant Examiner—Richard Hanig
Attorney, Agent, or Firm—Sheridan Ross & McIntosh

[57] ABSTRACT

A calibration method and apparatus for use in measuring the concentrations of components of a fluid is provided. The measurements are determined from the intensity of radiation over a selected range of radiation wavelengths using peak-to-trough calculations. The peak-to-trough calculations are simplified by compensating for radiation absorption by the apparatus. The invention also allows absorption characteristics of an interfering fluid component to be accurately determined and negated thereby facilitating analysis of the fluid.

40 Claims, 4 Drawing Sheets

U.S. PATENT DOCUMENTS

| | | | |
|---|---|---|---|
| 4,814,846 | 3/1989 | Matsumoto et al. | 357/30 |
| 4,816,889 | 3/1989 | Matsumoto | 357/30 |
| 4,831,454 | 5/1989 | Tanaka et al. | 358/213.31 |
| 4,866,293 | 9/1989 | Nakamura et al. | 250/578 |
| 4,879,470 | 11/1989 | Sugawa et al. | 250/578 |
| 4,914,719 | 4/1990 | Conlon et al. | 250/339 |
| 4,916,512 | 4/1990 | Ohmi et al. | 357/30 |
| 4,962,412 | 10/1990 | Shinohara et al. | 357/30 |
| 5,057,691 | 10/1991 | Kaihara et al. | 250/339 |
| 5,070,246 | 12/1991 | Durham et al. | 250/373 |

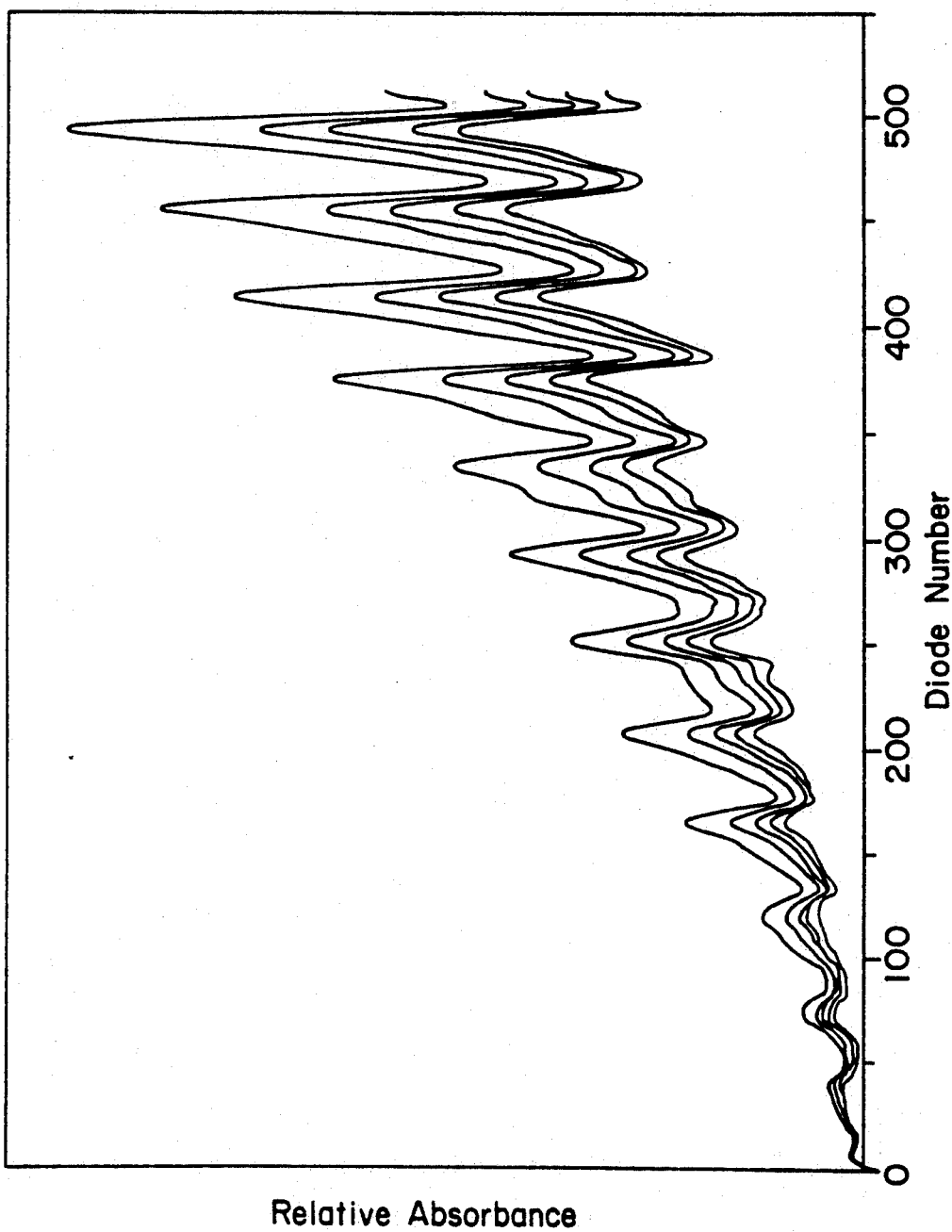

CALIBRATION METHOD AND APPARATUS FOR MEASURING THE CONCENTRATION OF COMPONENTS IN A FLUID

This invention was made with Government support under Contract No. DE-AC02-88ER80612 awarded by the Department of Energy. The Government has certain rights in this invention.

This is a continuation-in-part of U.S. patent application Ser. No. 07/410,925 filed on Sep. 22, 1989, now U.S. Pat. No. 5,070,246, which is incorporated by reference herein in its entirety.

FIELD OF THE INVENTION

The present invention is directed to the field of spectrometry, and in particular to a method and apparatus for calibrating spectrometer for measuring the concentration of components in a fluid.

BACKGROUND OF THE INVENTION

Spectrometers have been employed to determine the concentration, of fluids and to identify and determine the concentration of components found in mixtures of fluids. For example, the absorption characteristics of a gas at specific radiation wavelengths can be used to identify and quantify the concentration of the gas. This process can be modeled on the Beer-Lambert law, which states that the transmittance of radiation through a gas that absorbs radiation is decreased exponentially and proportional to the length of the radiation path and the concentration of the gas. This relationship is shown in Equation 1:

$$T = I/I_0 = e^{-acl} \qquad (1)$$

where:

T = transmittance of the radiation through the gas
$I_0$ = intensity of the radiation entering the gas
I = intensity of the radiation leaving the gas
a = molar absorptivity
c = concentration of the gas
l = distance the radiation beam travels through the gas The molar absorptivity, a, is dependent upon the wavelength of the radiation and upon the characteristics of the gas. The molar absorptivity indicates the degree to which a molecule will absorb radiation at a given wavelength. This can be determined by calibration on a given spectrometer. The molar absorptivity is a constant. Thus, once it is determined for a given spectrometer, it should theoretically not have to be determined again for that spectrometer.

In most spectrometers, it is not practical to measure the radiation intensities I and $I_0$ simultaneously. Therefore, the initial intensity, $I_0$, is determined by a measurement made during a calibration step in which all radiation absorbing gases are purged from the sample cell. For example, $I_0$ may be determined by a measurement made with only a zero gas, i.e., a gas which transmits substantially all radiation in a selected wavelength range, in the sample cell. The initial intensity, $I_0$ is the reference with which subsequent values are compared to determine the transmittance, T. However, using such a calibration process to determine $I_0$ may produce a source of error if the intensity of the radiation increases or decreases between the measurement of $I_0$ and the analysis of the unknown fluid, for example, if the intensity of the radiation source varies or if an impurity film layer coats the optical components.

In an alternative method, the radiation beam path can be alternated between a reference path and the sample path, as disclosed in U.S. Pat. No. 4,158,505 by Mathisen et al. issued Jun. 19, 1979. However, as can be seen from this patent, complicated mechanisms are required in order to provide for the switching of the beam between the reference and sample paths. Additionally, errors can be introduced if the reference and sample paths are not identical. For example, an impurity film layer may coat optical components in the sample path, but not in the reference path.

If more than one gas absorbs at the wavelength of interest, Beer's law dictates that the absorbance of a mixture is the sum of the absorbance of all the components of the mixture. U.S. Pat. No. 3,893,770 by Takami et al. issued Jul. 8, 1975, describes an apparatus for analyzing a plurality of mixed gases. The disclosed analyzer can measure component gases e.g. nitrogen dioxide ($NO_2$), sulfur dioxide ($SO_2$) and nitric oxide (NO), present in flue gases. It relies on detection of absorption spectra by simultaneous measurement of the intensity of radiation at several different discrete wavelengths. Interferences between spectra of different gases are compensated for by means of appropriate function generation and arithmetic units in the system's output circuitry. The interferences must be "irreversible" in order for the unit to operate. Additionally, a means must still be provided in order to obtain the initial reference intensity, $I_0$, in order to calculate the relative absorbance.

Another difficulty encountered in using an instrument of the type disclosed in U.S. Pat. No. 3,893,770 for characterizing components in flue gas is due to the environment in which the instrument has to operate. Since the instrument is measuring only a single wavelength of the spectrum for each gaseous component, any misalignment due to vibration or temperature or pressure gradients will produce inaccuracies in the measurement. In addition, the accuracy of the absorbance calculation is dependent upon the stability of the reference measurement. Since the reference measurement cannot be made continuously, any change in the output of the radiation source or distortion in the optics will produce a source of error.

In an article entitled "Development of Low Level $NH_3$ Measuring Method" by Nakabayashi et al., a method for measuring $NH_3$ at low concentrations is disclosed. In this method, the need for obtaining a reference intensity level, $I_0$, is eliminated. However, wavelength modulation of a certain angular frequency must be applied at a wavelength corresponding to an absorption peak. This requires the use of an oscillating mirror or slit. Such a moving mechanism in a spectrometer could be a source of error if the oscillation frequency were to deviate or the orientation of the mirror or slit were to become misaligned.

The Nakabayashi device is also very sensitive to temperature shifts and, therefore, must be housed in a constant temperature chamber and heated to a temperature of 43° C. Additionally, the sample path must be heated to a temperature of 300° C. in order to avoid the deposition of acid ammonium sulfate, which occurs below 250° C.

Therefore, it would be advantageous to measure the concentration of fluids in the presence of other interfering fluids.

It would also be advantageous to be able to measure the concentration of fluids continuously.

Furthermore, it would be advantageous to have a spectrometer assembly for measuring the concentration of components in a fluid with few moving parts.

In addition, it would be advantageous to provide a simple and accurate method for calibrating a spectrometer using the radiation transmitting or absorbing characteristics of a fluid based on the concentration of the fluid.

Also, it would be advantageous to provide a method and apparatus for measuring the concentration of components in a fluid which compensates for radiation absorption of the apparatus thereby simplifying calculations and/or increasing the accuracy of the measurements.

Further, it would be advantageous to have a spectrometer in which the accuracy of measurements is substantially unaffected by variations in radiation intensity due to variations in the intensity of the radiation source or changes in the spectrometer optics.

SUMMARY OF THE INVENTION

In accordance with the present invention, a method and apparatus for use in measuring the concentration of components in a fluid is provided.

According to an embodiment of the present invention, the measurement of at least one component in a fluid is provided. The method includes the steps of passing radiation through the fluid, measuring the amount of radiation which passes through the fluid at a plurality of different wavelengths within a wavelength range in which the component absorbs radiation, adjusting the amounts measured by compensating for wavelength-dependent variations in the amounts due to factors other than absorption of radiation by the fluid, and calculating the concentration of the component by performing a peak-to-trough measurement on a selected peak within the wavelength range based on the adjusted amounts.

Preferably, the step of adjusting the amounts measured comprises measuring the amount of radiation which passes through a zero gas at the plurality of points and determining a difference between the amounts of radiation which pass through the fluid at the plurality of points and the amounts of radiation which pass through the zero gas at the plurality of points. However, in contrast to methods where the intensity (I) is compared to a reference intensity ($I_0$) to determine concentration, the step of calculating the concentration of the component is accomplished by performing a peak-to-trough measurement on the set of adjusted amounts. The step of adjusting can also comprise performing a measurement with the radiation source turned off or substantially blocked, to obtain a "dark current" measurement, and determining a difference between the dark current measurement and the amounts of radiation which pass through the fluid at the plurality of points.

An apparatus constructed in accordance with an embodiment of the present invention includes a radiation source, a radiation detector for measuring the amounts of radiation transmitted through a fluid at a plurality of wavelengths within a selected wavelength range, a chamber positioned between the radiation source and the radiation detector, and a calculator. The calculator adjusts the measured amounts of radiation transmitted through the fluid by compensating for wavelength-dependent variations in the amounts due to factors other than absorption of radiation by the fluid, e.g., by subtracting reference amounts determined through measurements made with a fluid which transmits substantially all radiation in the selected wavelength range in the chamber and/or through measurements made with the radiation source turned off or substantially blocked. In addition, the calculator determines the concentration of a component of the fluid by performing a peak-to-trough measurement using the adjusted values.

According to another embodiment of the present invention, a method and apparatus for use in determining radiation-affecting characteristics of a fluid component is provided. The method includes the steps of introducing the fluid component into a chamber, passing radiation through the chamber, flowing a diluting fluid into the chamber, while allowing a mixture of the diluting fluid and the component to flow out of the chamber, and measuring the amount of radiation which passes through the chamber at a number of points within a wavelength range in which the component absorbs radiation at different times as the component is progressively diluted. For the measurements made at each of these times, the corresponding concentration of the component can be calculated by performing a peak-to-trough measurement on a selected peak within the selected wavelength range.

According to a further embodiment of the present invention, a method for substantially negating the effect of an interfering component of a fluid is provided. The method includes the steps of selecting (1) a first range of wavelengths in which the interfering component and at least one other component of the fluid absorb radiation, and (2) a second range of wavelengths in which substantially only the interfering component absorbs radiation. The amount of radiation which passes through the interfering component at a number of points within the first range and at a number of points within the second range is determined for various concentrations of the interfering component. The measurements for the various concentrations are obtained by flowing the component into a chamber, diluting the component with a diluting fluid, and obtaining the measurements at different times as the component is progressively diluted. The amount of radiation which passes through the fluid at a number of points within the first range and at a number of points within the second range is measured and the measured amounts of radiation passing through the fluid in the second range are matched to the determined amounts of radiation passing through the interfering component in the second range. The method further comprises the step of determining a difference between measured amounts of radiation passing through the fluid in the first range and corresponding determined amounts of radiation passing through the interfering fluid in the first range.

According to a still further embodiment of the present invention, an apparatus for use in determining radiation-affecting characteristics of a fluid component at a plurality of concentrations of the component is provided. The apparatus comprises a radiation source, a chamber, means for introducing a quantity of the component into the chamber, means for flowing a diluting fluid into the chamber and concurrently flowing a mixture of the diluting fluid and component out of the chamber, and radiation detection means capable of sensing the intensity of radiation within a selected wavelength range at a plurality of times as the component is progressively diluted by the diluting fluid. Preferably, the fluid is a gas and the diluting fluid is a zero gas which transmits substantially all radiation in the selected wavelength range. Alternatively, a vacuum can be employed instead of a zero gas.

BRIEF DESCRIPTION OF THE DRAWINGS

FIG. 2 illustrates a plurality of spectra for $SO_2$ corresponding to a plurality of concentrations.

DETAILED DESCRIPTION OF THE INVENTION

A device in accordance with an embodiment of the present invention is designed to measure the concentration of components in a fluid. Preferably, the device measures the concentration of gaseous components in a gas.

A preferred embodiment of the device provides a quantitative measurement of ammonia ($NH_3$) in a gas in the presence of interfering gases such as sulfur dioxide ($SO)_2$ nitric oxide (NO).

Figure 1:
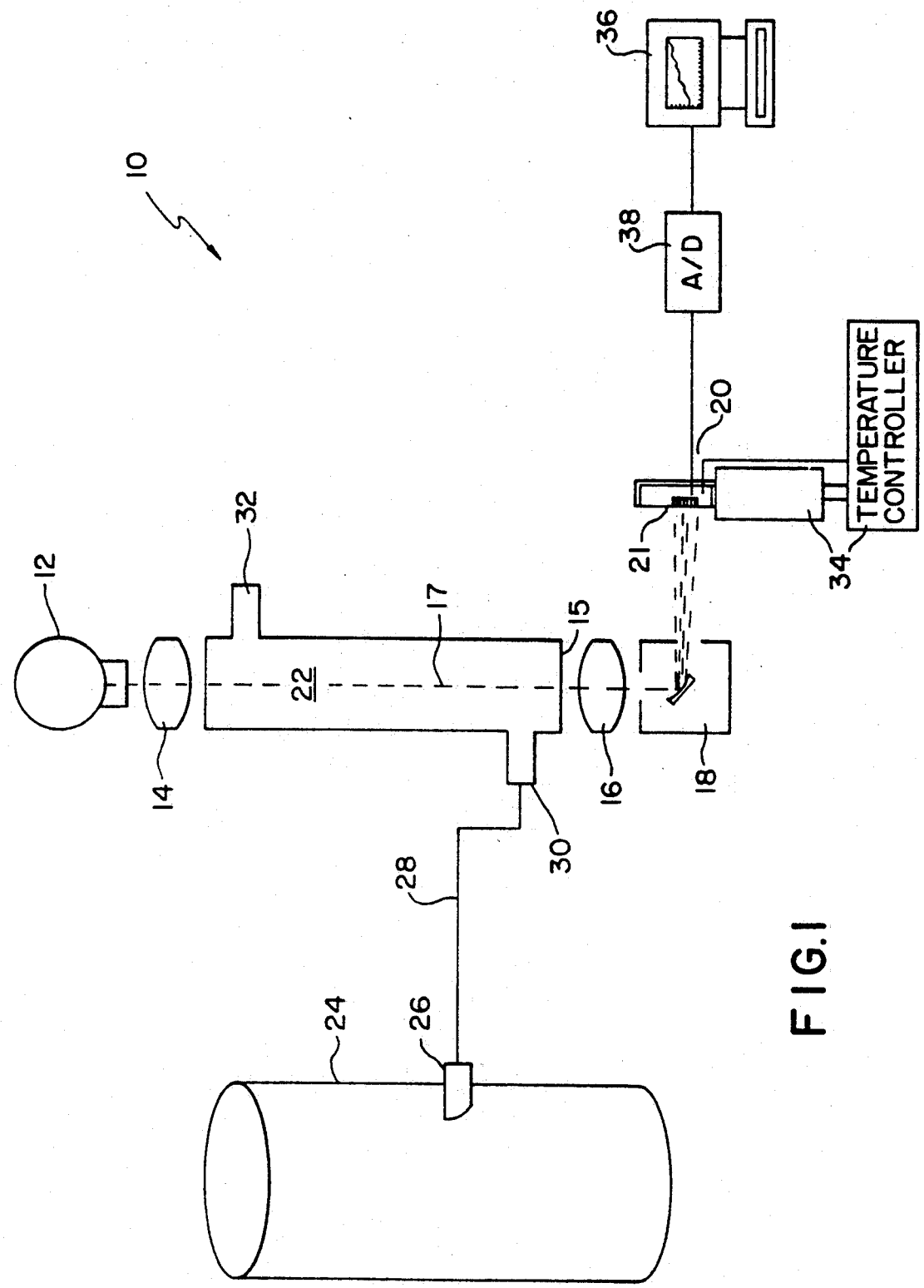
FIG. 1 illustrates a preferred embodiment of an extractive spectrometer in accordance with the present invention.

A preferred embodiment of the present invention is illustrated in FIG. 1. An instrument 10 includes a radiation source 12. Preferably, the radiation source 12 is a source of ultraviolet and visible radiation in the wavelength region of 1900 to 6000 Angstroms. The radiation source 12 is energized by a power supply (not shown) designed to provide a constant current. Sufficient optics, including lenses 14 and 16, as well as mirrors (not shown) and windows 15 are provided to focus the radiation beam 17 from the radiation source 12 at the entrance to a polychromator 18. Preferably, the polychromator 18 comprises a prism or an optical grating as well as internal means whereby the radiation is collimated and focused, as appropriate. The polychromator 18 disperses the radiation 17 from the radiation source 12 across a radiation detector 20. The polychromator 18 can be physically adjusted to provide analysis of more than one wavelength region of interest. The wavelength resolution of the instrument 10 is defined by the optics, particularly optics within the polychromator 18 and the detector 20, and the geometric spacing between the polychromator 18 and the radiation detector 20.

The radiation detector 20 preferably includes a charge coupled device such as a linear photodiode array 21, which is placed across the focal plane of the polychromator 18. A linear photodiode array is a large scale, integrated circuit fabricated on a single monolithic silicon crystal. It consists of an array of diodes, or pixels, each acting as a radiation-to-charge transducer and a storage device. Linear photodiode arrays are well suited for use in ultraviolet spectrometers because they have a large quantum efficiency, e.g. 40% to 80%, throughout the ultraviolet range as well as geometric, radiometric, and electronic stability. Linear photodiode arrays are very tolerant of humidity, vibration and electromagnetic fields.

The linear photodiode array 21 is located in the focal plane of the polychromator 18 so that each diode corresponds to a particular wavelength resolution of the spectrum produced by the polychromator 18. The linear photodiode array 21 provides an efficient sensor for the digital acquisition of spectra, because the array 21 itself, by its presence in the focal plane of the polychromator 18, digitizes the spectrum into discrete intervals corresponding to wavelengths. Unlike scanning spectrometers of the prior art, whose wavelength accuracy is mechanically limited, the linear photodiode array spectrometer is limited only by geometric constraints of the detector itself, by vibration and thermal expansion of the optical components, and by the stability of the radiation source 12. Wavelength accuracy is equivalent to diode spacing multiplied by the linear dispersion of the polychromator. The geometric registration and, therefore, its wavelength accuracy and precision, are typically better than mechanically scanned spectrometers. The linear photodiode array 21 is also advantageous in that it provides an instantaneous spectrum which can be used for determining the gas concentration of different gases. Preferably there are from about 500 to about 1000 individual linear photodiodes in the array, with a center-to-center distance of about 25 micrometers between each diode.

The resolution of the photodiode array plays an important role in the accuracy of the instrument. Therefore, the appropriate resolution for any given instrument will be determined in part by the desired accuracy. For present purposes, the resolution will be expressed in terms of "wavelength (measured in Angstroms) per diode." It has been found that if the resolution is too low (i.e., the wavelength per diode value is too high) interference between adjacent peaks of a spectrum may result. However, if the resolution is too high (i.e., the wavelength per diode value is too low), then the range of wavelengths which fall upon the entire photodiode array will be too small to be useful. It has been found that for the measurement of gases such as $NH_3$, $SO_2$ and NO, a resolution between about one Angstrom per diode and four Angstroms per diode works satisfactorily. A resolution of one Angstrom per diode is preferred for measuring the concentration of these three gases.

The fluid to be analyzed must be positioned between the radiation detector 20 and the radiation source 12. The polychromator 18 can be placed either before, after or within the fluid. An extractive measurement approach, as illustrated in FIG. 1, involves the use of a gas cell 22 with windows 15 at each end. Preferably the windows 15 are made of a material which is highly transparent to ultraviolet radiation, e.g., fused silica or quartz glass, and are positioned horizontally to reduce the likelihood of accumulation of particulate matter. A sample of fluid, e.g. flue gas from a stack 24 (not to scale), is extracted by means of a probe 26 or tube such as a venturi tube and transported to the gas cell 22 through a sample line 28. The gas sample then flows through the inlet 30 of the gas cell 22 where it is analyzed. The sample probe 26, sample line 28 and gas cell 22 can be heated to an appropriate temperature to prevent condensation and reactions between various components from occurring. The gas sample exits from the gas cell 22 via outlet 32.

In a preferred embodiment, a temperature controlled cooler 34 is connected to the radiation detector 20 to provide a means to maintain a constant temperature for the detector 20, independent of fluctuations in the ambient conditions. Linear photodiode arrays are manufactured from a silicon based substrate and their performance is affected by changes in operating temperature. Thermally-generated dark current represents a source of noise for linear photodiode array systems. The net effect of the dark current for uncooled or insufficiently cooled arrays is high noise in low-radiation-level situations or when strongly absorbing samples are present. Dark current at long integration times, or for uncooled arrays, can rapidly reduce the maximum measurable signal.

A microprocessor 36 is employed to process the signals from the detector 20 to determine the concentration of component gases. An analysis program employing various algorithms, as described in more detail hereinbelow, is used to measure the intensity of transmitted radiation, account for variations in the measured intensity due to factors other than absorption of radiation by fluids (e.g. due to system optics or due to dark current), account for changes in the intensity of the radiation, account for interferences, and check alignment.

In a preferred embodiment, each photodiode of the linear photodiode array 21 is connected to the output line of a field effect transistor (FET) switch, which is controlled by a single bit that is shifted through a shift register. When the FET switch is addressed, the diode is charged up to its full reverse-bias potential. The charging of each diode takes less than a microsecond; the multiplexer switching between elements occurs at a rate of 250 to 2000 kHz, depending upon the limitations of the analog/digital converter 38. The readout from the detector 20 is accomplished through the use of two transistor-transistor logic (TTL) level signals, a start pulse signal and a clock signal.

The analog signal from the common output line of the detector 20 is run through an amplifier sample-and-hold system to reduce noise. It is then digitized and transmitted to a microprocessor 36. The data can then be read out in real-time. This maximizes the amount of data that can be processed. Various techniques, such as variable integration, diode grouping, or diode skipping, optimize the data collection relative to the analog/digital range, signal to noise ratio, and available digital memory, respectively.

With the present device 10 it is not necessary to compare the signal to a reference measurement (intensity value for zero gas, $I_0$, taken at another period of time) to determine the gas concentration. From Equation 1 it can be seen that the concentration is linearly related to log I. With the present spectrometer and method it is possible to use the log of the intensity, I, at two points within a wavelength range to determine the concentration. However, in accordance with one embodiment of the present invention, it has been discovered that a reference measurement taken at infrequent intervals (e.g., once per day) can be useful in simplifying and/or increasing the accuracy of concentration calculations. Although the relationships will be described in terms of log values, one skilled in the art will appreciate that other relationships, including direct measurements and ln values, can also be used.

An analysis program is employed to calculate the concentration of component gases. In one embodiment, the analysis program first scans a given spectrum, i.e., set of values indicative of the amount of radiation which passes through the gas across a wavelength range. The analysis program then subtracts from the given spectrum a dark current measurement made with the radiation source 12 blocked, e.g., turned off or closed off by a shutter. In addition, the program subtracts from the given spectrum a reference spectrum made with a fluid which transmits substantially all radiation in the selected wavelength range (as will be described below). The program then determines the change in log intensity between a minimum (peak) and a maximum (trough) of the resulting spectrum within the selected wavelength range. The minimum intensity is referred to as a "peak" because a low intensity is indicative of a high, or peak, absorbance. The minimum intensity therefore appears as an absorbance peak in log space as shown in FIGS. 3(c) and 3(e).

The change in log intensity or "peak-to-trough height" can then be plotted against the known concentration to form a calibration curve. A similar procedure is followed for an unknown concentration of the gas. The peak-to-trough height for the unknown concentration is compared to the calibration curve in order to determine the concentration. Naturally, this process can be programmed to be performed by a computer, using algorithms rather than actual plotted curves. This approach eliminates the need for an initial reference intensity, $I_0$, and simplifies and speeds the calculation of concentration. Since the analysis procedure searches for characteristic features of the absorption spectrum (i.e. peak and trough) rather than transmittance at some preselected, fixed wavelength, equipment deviations, such as drift and lamp intensity fluctuations can be compensated for automatically.

It will be appreciated that any type peak-to-trough measurement by which the selected peak can be characterized can be used to calculate concentration. For example, the peak-to-trough measurement can be determined by first finding the minimum transmitted radiation value at a first wavelength within a preselected wavelength range, then measuring the difference between this minimum value and either a maximum transmitted radiation value within the range or a transmitted radiation value at a second wavelength which differs from the first wavelength by a set amount. Alternatively, the peak-to-trough measurement can be calculated by first generating a base line and then measuring the difference between the minimum transmitted radiation value (i.e. the peak) and this base line at the wavelength of the peak. Similarly, the peak-to-trough measurement can be calculated by first generating a baseline and then measuring the area enclosed by the baseline and the absorption spectrum, or an area bounded by the baseline and the spectrum across a selected wavelength range which includes the peak wavelength. Of course, the peak-to-trough measurements may be performed by a computer using algorithms rather than actual plotted curves.

In the "baseline" methods, the minimum transmitted radiation value is first determined within the selected wavelength range. Examples of preferred selected wavelength ranges for specific gases are: between about 2040 Angstroms and about 2120 Angstroms for $NH_3$, between about 2100 Angstroms and about 2200 Angstroms for NO and between about 2270 Angstroms and about 2300 Angstroms for $SO_2$. In an alternative embodiment, the preferred selected wavelength ranges for specific gases are: between about 2040 Angstroms and about 2120 Angstroms for $NH_3$, between about 2200 Angstroms and about 2300 Angstroms for NO, and between about 2170 Angstroms and about 2200 Angstroms for $SO_2$.

Appropriate algorithms can be employed to automatically determine the minimum transmitted radiation in the selected range of wavelengths. After the minimum transmitted radiation is determined, two groups of transmitted radiation values are selected at wavelengths above and below the wavelength of the minimum transmitted radiation. A linear regression operation is performed on the two groups of points in order to produce the base line. In accordance with the first type of baseline method described above, the log value of the distance between the minimum transmitted radiation value and the base line is then determined at the wavelength at which the minimum transmitted radiation occurred. This log value is employed to calculate the concentration. According to an "area" type method, the area between the baseline and spectrum can be determined mathematically. For example, where the instrument 10 employs a linear photodiode array 21, an area measurement can be obtained by first multiplying the log value of the distance between the spectrum radiation value and the baseline at each array element by the wavelength width of the element to obtain a product corresponding to each element, and then adding the products for each element across the selected range. This area measurement can then be employed to calculate the concentration.

As stated above, a reference spectrum made with an evacuated chamber or other medium which transmits substantially all radiation in a selected wavelength range (e.g., a zero gas), may be subtracted from a spectrum made with an unknown fluid before determining a concentration of a component of the unknown fluid according to any of the techniques described above. For example, the gas cell 22 or other chamber may be purged of radiation absorbing gases once a day so that the reference spectrum can be obtained. This purging may be accomplished, for example, by flowing a zero gas such as $N_2$ into the chamber, by evacuating the chamber or by selective chemical scrubbing. In this manner, wavelength dependent variations in the measured radiation intensity due to factors other than the absorption characteristics of the fluid can be reduced or eliminated. For example, the apparatus optics such as the lenses 14 and 16, the optics within the polychromator 18 and the detector 20 and the windows of the gas cell 22, may transmit radiation more efficiently towards one end of the selected wavelength range, resulting in a slope or other irregularity in the measured spectrum which is due to characteristics of the spectrometer optics rather than the absorbance characteristics of the fluid. Similarly, the measured spectrum may be affected by the frequency response characteristics of the diodes. Thus, by subtracting a reference spectrum made with a zero gas from the spectrum made with the unknown fluid, a flatter spectrum may be obtained thereby simplifying the calculations involved in determining concentration and potentially increasing the accuracy of the concentration calculation. For example, errors may result, as the analysis program scans across a wavelength range to find a peak, if the unknown fluid spectrum contains a slope due to factors other than radiation absorption by the unknown fluid. Of course, a mathematical relationship approximating the effect of the reference spectrum may be used in place of actual reference spectrum values in the spectral subtraction step.

Figure 3A:
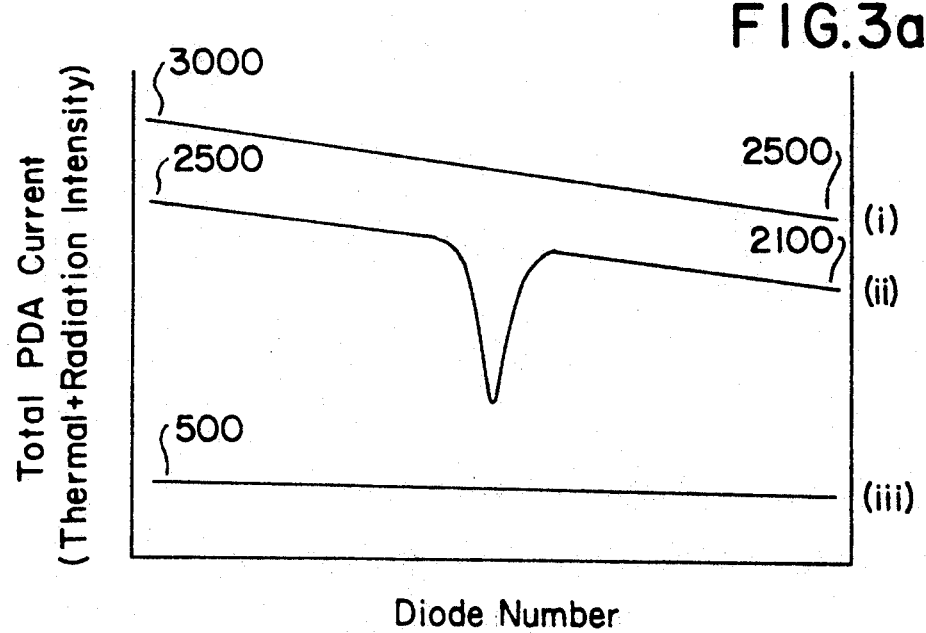
FIG. 3(a) illustrates spectra for a zero gas and an absorbing fluid, and a dark current measurement.

An exemplary zero gas reference spectrum is plotted in FIG. 3(a) (spectrum i). The downward slope of this spectrum is not due to absorbance by a gas but instead results from the measured transmittance characteristics of the instrument 10. The wavelength may decrease from the lower photodiode element numbers to the higher numbers or the wavelength may increase. In FIG. 3(a), if the wavelength is taken to decrease from the lower photodiode element numbers to the higher numbers, it is observed that the measured intensity is greater at longer wavelengths. Such a phenomenon may be observed, for example, if the optical elements are more efficient at transmitting longer wavelength radiation. It is to be understood that a measured spectrum may have a slope different from that of spectrum (i).

The present technique may be contrasted to techniques which use an initial reference intensity, $I_0$, to determine concentration. Such systems may produce a source of error if the intensity of the radiation source increases or decreases or if the optics become fouled between the measurement of the zero gas and the analysis of the unknown fluid. According to the present method, it is possible to use the log of the intensity, I, at two points within a wavelength range or an area measurement to determine the concentration. The reference spectrum made with the zero gas is simply subtracted from the spectrum made with the unknown fluid before calculating the concentration so that the calculations can be performed on a flatter spectrum. The calculation will be substantially unaffected if the intensity of the radiation source changes, or if the optics become fouled, between the measurement of the zero gas and the analysis of the unknown fluid because the calculation does not directly compare the intensity, I, to a reference intensity, $I_0$, to determine concentration.

An important advantage is that the present method and apparatus determines the minimum transmitted radiation within the selected wavelength range. Therefore, if for some reason the spectrum shifts relative to the photodiode array, the device is self-correcting. In other words, once the minimum is found, the software assigns this value the designation of the "peak value." The trough values are then selected relative to the peak value. A second derivative analysis can be used to locate the peak. The peak value can be thought of as being a "characteristic feature," around which the rest of the calculations are based. Because the program is designed to search out the peak value within a range, if the spectrum on the photodiode array shifts to the left or right, but remains in this range, the program is capable of automatically correcting for the shift without requiring mechanical calibrations. In this regard, it has been found sufficient to base the calculations on a daily measured peak wavelength for a selected peak of a particular gas, e.g., a peak value for the NO peak in the 2200-2300 angstrom range can be measured once per day and used as the characteristic feature for all measurements that day.

It should be noted that although transmission values are discussed in terms of their respective wavelengths, in fact the computer program can correlate the transmitted radiation values to a photodiode array number rather than an actual wavelength. It makes no difference if the analysis program is searching for the characteristic feature, i.e. the peak, within a given range of wavelengths or within a given range of photodiode numbers as the photodiode numbers are related to wavelengths in a known manner. Any convention can be employed, as long as they define a range.

In summary, the information provided to the analysis program in order to calculate concentrations preferably includes: (1) a calibration curve or an equation defining a calibration curve, (2) a selected range, e.g. wavelength range, in which to search for a minimum transmitted radiation value, (3) a dark current measurement made with the radiation source turned off or substantially blocked, (4) a reference spectrum made with a fluid which preferably transmits substantially all radiation within the selected range or with an evacuated chamber, and (5) instructions regarding how to determine the trough transmitted radiation value. The reference spectrum and dark current measurement may be obtained, for example, on a daily basis. As explained hereinbefore, the trough, or maximum transmitted radiation value, can be determined by merely finding the transmitted radiation value at a given wavelength distance away from the minimum transmitted radiation value (i.e., the peak). Alternatively, the trough can be determined by finding the maximum value in the selected wavelength range. In yet another alternative, a base line can be generated and the difference between the minimum value and the base line at a given wavelength can be determined. According to a further alternative, an area defined by a baseline and a transmitted radiation spectrum across a wavelength range including a selected peak can be determined.

Referring to FIGS. 3(a) through 3(e), an example is provided to illustrate various concepts and steps described above. Each of the figures illustrate exemplary spectra across a wavelength range represented by a range of diode numbers. FIG. 3(a) shows spectra for a zero gas (spectrum i) and a fluid which absorbs radiation within the selected range (spectrum ii), and a dark current measurement (measurement iii) all plotted against the output of the photo diode array. Thus, the zero gas spectrum is depicted as a substantially linear spectrum sloping from a maximum value of approximately 3,000 units, wherein a unit is proportional to the voltage at the relevant photodiode element and the analog-to-digital gain of the associated electronic circuitry, at the lower end of the wavelength range to approximately 2,500 units at the upper end of the range. The absorbing fluid spectrum is a generally sloping spectrum with a single absorbance peak. The dark current measurement is depicted as being substantially linear. It is to be understood that, in the practice of the present invention, the actual spectra/measurements obtained may vary substantially from those depicted, e.g., the zero gas spectrum and dark current measurement may be non-linear.

Figure 3B:
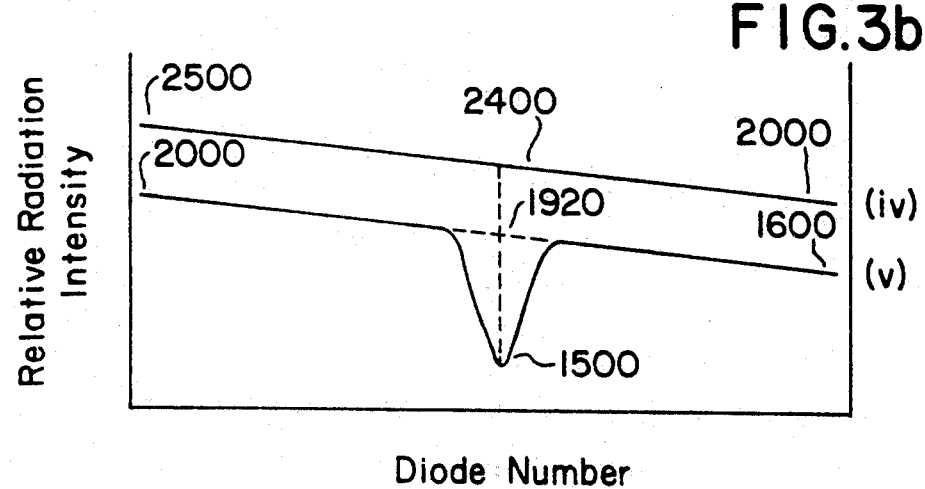
FIG. 3(b) illustrates spectra for the zero gas and the absorbing fluid with the dark current measurement subtracted therefrom.
Figure 3C:
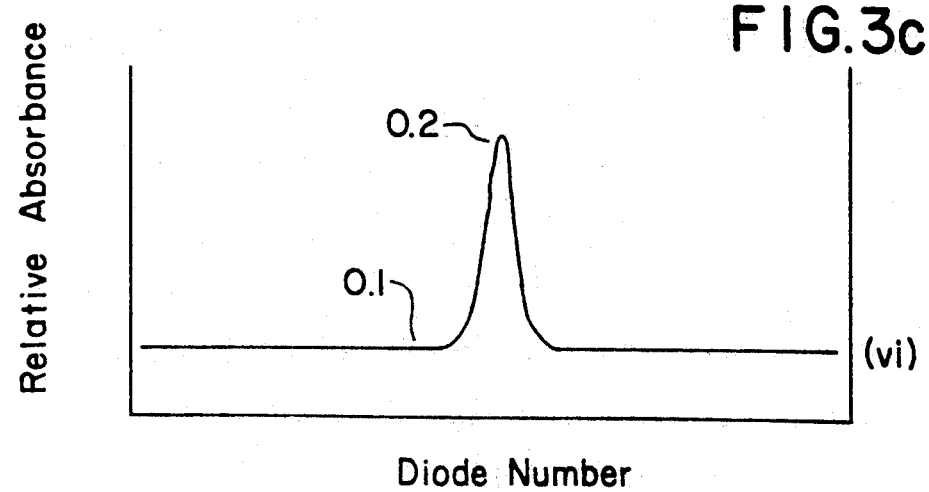
FIG. 3(c) illustrates an absorbance spectrum.

FIG. 3(b) depicts relative radiation intensity spectra for the zero gas, $I_{ref}$, and for the absorbing fluid, I, obtained by subtracting the dark current measurement from the zero gas and absorbing fluid spectra (spectra iv and v, respectively). As illustrated, the absorbing fluid intensity spectrum has a peak of 1,500 units and a trough of 1,920 units as computed by a baseline method. FIG. 3(c) shows an absorbance spectrum (spectrum vi) which is obtained by converting the I and $I_{ref}$ values at each diode into radiation absorbance (absorbance=log $I_{ref}$−log I). Thus, at the peak of this spectrum, the absorbance is: log (2,400)−log (1,500)=0.2. The absorbance at the trough is: log (2,400)−log (1,920)=0.1. The peak-to-trough difference is, therefore, 0.2−0.1=0.1.

Figure 3D:
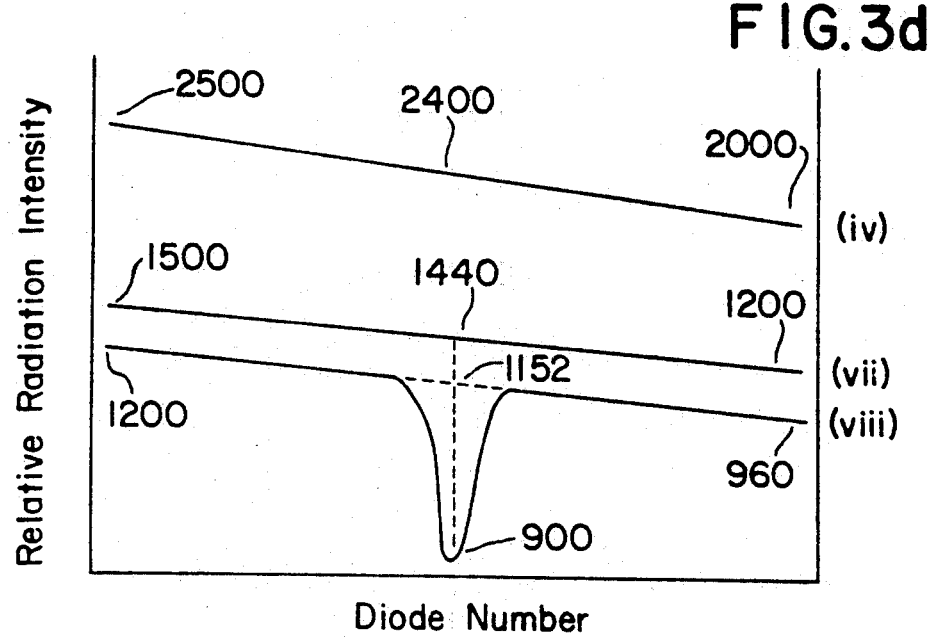
FIG. 3(d) illustrates spectra for a zero gas and an absorbing fluid.
Figure 3E:
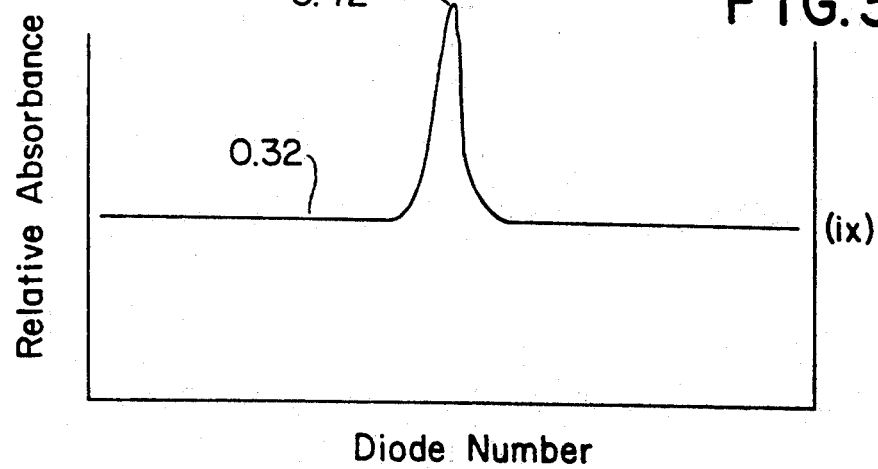
FIG. 3(e) illustrates an absorbance spectrum.

FIGS. 3(d) and 3(e) show that the accuracy of the concentration calculation is substantially maintained even if the zero gas and absorbing fluid spectra change, e.g., the intensity of the radiation source changes or the optics become dirty. Spectrum vii depicts a shifted zero gas spectrum, relative to spectrum iv, due to such a phenomenon. Thus, for example, spectrum iv may represent a daily zero gas measurement whereas spectrum vii represents a theoretical zero gas measurement made at the same time as the absorbing fluid spectrum (spectrum vii). Because overall radiation intensity is diminished, the spectrum for the absorbing fluid is also shifted as indicated by intensity spectrum viii. The absorbance at the peak of spectrum viii is: log (2,400)−log (900)=0.42. The absorbance at the trough of spectrum viii is: log (2,400)−log (1,152)=0.32. The peak-to-trough difference, as shown on absorbance spectrum ix, is thus 0.42−0.32=0.1, which is the same value as obtained above.

As already pointed out, in the present method it is useful to know the minimum transmitted radiation value within a selected range, and at least one local maximum value at wavelengths above and/or below the wavelength of the minimum value. The maximum and minimum values can be determined by any method available to those skilled in the art. For example, a function approximating the spectral curve can be determined and maximum and minimum values can be calculated from the first and second derivatives of the function or an area defined by reference to the curve can be calculated, using well known techniques.

The analysis program can be designed to perform spectral subtractions in order to account for interferences between multiple components in an unknown fluid. A spectrum indicative of the effect of the interfering fluid may be obtained from a stored library file or determined by a calibration procedure, as described below, and subtracted from a spectrum made with the unknown fluid to facilitate analysis of other components of the unknown fluid. Alternatively, the subtraction can be performed chemically such as by selective scrubbing.

In order to enhance the accuracy of the present method and apparatus, a spectrum corresponding solely to the interfering fluid component should be accurately determined so that the effect of the interfering component can be substantially negated by spectral subtraction. However, the spectrum of the interfering component will vary with the concentration of the component. Therefore, it is desirable to obtain a specific spectrum which accurately corresponds to the concentration of the interfering component.

According to the present invention, a plurality of spectra corresponding to a plurality of concentrations of the interfering component may be easily and efficiently obtained and used to substantially negate the effect of the interfering component. Initially, a calibration curve relating a peak-to-trough measurement at a selected peak to concentration may be obtained for the interfering component using a technique as described above. This may be accomplished by performing a peak-to-trough measurement on the selected peak at a plurality of concentrations within a selected concentration span, i.e., range of concentrations within which the interfering gas is to be calibrated, and then performing an appropriate regression analysis to fit a calibration curve to the values measured. For example, a calibration curve for $SO_2$ (which has been found to yield a substantially linear calibration curve) in the span from 0-100 ppm may be obtained by performing peak-to-trough calculations at an appropriate wavelength range with (1) the gas cell 22 or other chamber substantially purged of $SO_2$, and (2) a concentration of 100 ppm of $SO_2$ introduced into the gas cell 22 or other chamber. The $SO_2$ concentration for subsequent spectra can then be quantified using the established calibration curve. Introduction of the desired concentrations may be accomplished by flowing the interfering component into the chamber, e.g., by opening a valve such as a solenoid valve to allow flow of the interfering component until a stable concentration is achieved and then closing a valve to stop the flow.

After the upper end of the concentration span is attained, e.g., 100 ppm of $SO_2$ are introduced into the gas cell 22 or other chamber, a diluting fluid may be introduced into the gas cell 22 or other chamber while a mixture of the diluting fluid and the interfering component are flowed out of the gas cell 22 or other chamber to dilute the interfering component. For example, a zero gas such as $N_2$ can be flowed into the gas cell 22 by opening a valve such as a solenoid valve and, concurrently, a second valve can be opened to allow escape of gas from the gas cell 22. It will be appreciated that the gas escaping from the gas cell 22 will comprise a mixture of the diluting gas and the interfering component. A family of spectra may thereby be obtained by measuring the amount of radiation which passes through the gas cell 22 at each photodiode element, at a number of times as the interfering component is progressively diluted. An appropriate rate of flow of the zero gas into the gas cell 22 or other chamber may be selected to allow the desired number of spectra to be obtained and stored. FIG. 2 shows characteristic spectra for a plurality of concentrations of $SO_2$. The spectra were plotted as log radiation intensity versus photodiode element number because the concentration is proportional to the log of the radiation intensity and the element numbers corresponding to wavelengths. As described above, the diode number is indicative of a discrete wavelength or range of wavelengths within the selected range.

The stored spectra may be used to calibrate the effect of the interfering component at a plurality of wavelengths within the selected range, for example, at each diode. The spectra provide a plurality of values indicative of the amount of radiation which passes through the interfering component at a plurality of concentrations (as indicated by performing a peak-to-trough calculation on an appropriate peak for each spectrum) for each diode. These values may be stored for use in spectral subtraction or, where greater accuracy is desired, a curve fitting procedure may be performed on the values stored for each diode to obtain interim values indicative of the amount of radiation which passes through the interfering component for interim concentrations of the interfering component. The curve fitting procedure may comprise, for example, determining a mathematical relationship, such as by performing a multiple regression analysis, expressive of the relationship between the amount of radiation passing through the interfering component and the concentration of the interfering component for each diode. Of course, such a mathematical relationship may relate the amounts of radiation passing through the interfering component directly to a peak-to-trough measurement rather than to the concentration thereby indicated. The foregoing stored spectra/curve fitting procedure may be performed, for example, on a daily basis.

Stored spectra may be used to substantially negate the measured effect of an interfering component as follows. A family of spectra are obtained for the interfering component, as described above, which spectra include a plurality of points in a first wavelength range, wherein the interfering component and at least one other component of the unknown fluid absorb radiation, and a plurality of points in a second wavelength range wherein substantially only the interfering component absorbs radiation. A peak-to-trough measurement can then be performed on a peak within the second range for each of the spectra. This measurement or the corresponding concentration of the interfering gas can be used to identify each spectrum. It will be appreciated that similar values may be used to define and identify intermediate spectra (or set of intermediate values at corresponding concentrations) where a curve fitting procedure is employed. These spectra are then stored for use in the analysis program to perform spectral subtraction.

The apparatus 10 may then be used to obtain a spectrum for the unknown fluid which spectrum includes a plurality of points in both the first and second wavelength range. For example, if it is desired to negate the interfering effect of $SO_2$ in a fluid containing both $SO_2$ and $NH_3$, the first wavelength range may be from about 2040 Angstroms to about 2120 Angstroms and the second wavelength range may be from about 2270 Angstroms to 2300 Angstroms. A peak-to-trough measurement can be performed on a peak of the unknown fluid spectrum in the second range and used to compare the spectrum to the stored spectra to identify a spectrum having a corresponding peak. As will be understood from the description above, because the peak-to-trough measurement is indicative of concentration, the spectra may be compared by peak-to-trough values, by the indicated concentrations, or by other representative values. The analysis program can then be employed to calculate a difference between the measured spectrum for the unknown fluid and the corresponding spectrum for the interfering component so that the measured effect of the interfering component can be substantially negated. It is important to note that in this spectral subtraction step, the analysis program calculates differences at corresponding wavelengths as determined by reference to an appropriate peak rather than at corresponding photodiode elements. Thus, substantially no error is introduced if for some reason the interfering component spectrum shifts relative to the photodiode array.

It should be noted that in order for the spectral subtraction technique to perform adequately, the baseline slope of the radiation passing through the fluids must remain substantially constant, or vary in a known manner. If the baseline slope fluctuates in an unknown manner, error can be introduced when subtracting the interfering component spectrum from the unknown fluid spectrum. The reason for this is that, although the concentration is calculated based on a peak-to-trough measurement, the reference interfering component spectra are only meaningful if the baseline radiation intensities are known.

In summary, according to an embodiment of the present invention, the steps involved in substantially negating the effect of an interfering component can include: 1) obtaining a calibration curve for the component, 2)

obtaining and storing a plurality of spectra for the component as the component is progressively diluted by a zero gas, 3) using the stored spectra and calibration curve to derive mathematical equations from which a spectrum for a particular concentration of the component may be approximated, 4) obtaining a spectrum for an unknown fluid including the interfering component, 5) identifying the concentration of the interfering component in the unknown fluid by performing a peak-to-trough measurement in a wavelength range where substantially only the interfering component absorbs radiation, and 6) determining a difference between the measured spectrum of the unknown fluid and a determined spectrum for the interfering component corresponding to the concentration of the component in the unknown fluid. It will be appreciated that the steps of obtaining a calibration curve, obtaining and storing the plurality of spectra, and deriving the mathematical equations can be performed on a daily basis. Thus, a peak-to-trough measurement in a wavelength range where only the interfering component absorbs radiation can be used to determine and negate the effect of the interfering component at wavelengths where the interfering component and at least one other component of the fluid absorb radiation. It is an advantage of the present invention that the effect of the interfering component can be easily and accurately determined and negated.

As will be appreciated by those skilled in the art, the present method and apparatus can be used on non-gaseous systems. For example, the present apparatus and method can be used to perform spectroscopic analysis on liquids. Additionally, although the present invention has been described with specific embodiments employing absorbance in the ultraviolet region, absorbance in other wavelength regions can be employed with equal results.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A method for measuring at least one component in a fluid, comprising the steps of:
   (a) passing radiation through said fluid;
   (b) measuring amounts of radiation which pass through said fluid at a plurality of wavelengths within at least one wavelength range in which said component absorbs radiation;
   (c) adjusting said amounts measured by compensating for wavelength dependent variations in said amounts due to factors other than absorption of radiation by said fluid; and
   (d) calculating the concentration of said component by performing a peak-to-trough measurement on a selected peak within said range based on the adjusted amounts.

2. The method of claim 1, wherein said step of adjusting comprises:
   passing radiation through a medium which transmits substantially all of said radiation within said selected range; and
   measuring amounts of radiation which pass through said medium at a plurality of wavelengths within said range.

3. The method of claim 2, wherein said medium comprises a zero gas.

4. The method of claim 2, wherein said step of adjusting comprises:
   determining a difference between the measured amounts of radiation which pass through said medium at said plurality of wavelengths and the measured amounts of radiation which pass through said fluid at said plurality of wavelengths.

5. The method of claim 2, wherein said step of adjusting comprises
   determining a relationship between the amounts of radiation which pass through said medium and the wavelength of said radiation; and
   determining a difference between the amounts of radiation which pass through said medium at said selected points as indicated by said relationship and the measured amounts of radiation which pass through said fluid stream at said selected points.

6. The method of claim 1, wherein said fluid is a flue gas from a smoke stack.

7. The method of claim 1, wherein said component is selected from the group consisting of NO, $SO_2$, $NH_3$, aromatic hydrocarbons, formaldehyde, ozone, chlorine and bromine.

8. The method of claim 1, wherein said step of calculating the concentration of a component comprises:
   determining a difference between two points within said range based on the adjusted amounts.

9. The method as claimed in claim 1, wherein said step of calculating the concentration of the component comprises:
   (a) determining a first wavelength at which minimum transmitted radiation occurs within said selected range;
   (b) determining a second wavelength at which maximum transmitted radiation occurs within said selected range;
   (c) determining the difference between said minimum transmitted radiation and said maximum transmitted radiation; and
   (d) calculating the concentration of said component using reference data obtained from measurements performed on gases of known concentration.

10. The method of claim 1, wherein said step of calculating the concentration of a component comprises:
    (a) determining a first wavelength at which a minimal amount of radiation is transmitted within said selected range;
    (b) calculating a base line by performing a regression calculation on two groups of transmitted radiation values within said selected range, the first group of transmitted radiation values corresponding to wavelengths less than said first wavelength and at which high transmission occurs and the second group of transmitted radiation values corresponding to wavelengths greater than said first wavelength and at which high transmission occurs;
    (c) determining the difference between said minimal transmitted radiation value and said base line at said first wavelength; and
    (d) calculating the concentration of said component using reference data obtained from measurements performed on fluids of known concentration.

11. The method of claim 1, wherein said step of calculating the concentration of a component comprises:
    (a) calculating a baseline based on the measured amounts of radiation;

(b) determining an area between a spectrum defined by said measured amounts and said baseline, and between a first wavelength and a second wavelength, wherein said first wavelength is less than the wavelength of said peak and said second wavelength is greater than the wavelength of said peak; and (c) calculating the concentration of said component using reference data obtained from measurements performed on fluids of known concentration.

12. The method of claim 1, wherein at least two wavelength ranges are selected in order to measure at least two components in said fluid.

13. The method of claim 1, wherein the concentration of $NH_3$ in a fluid is measured and the selected wavelength range is from about 2040 Angstroms to about 2120 Angstroms.

14. The method as claimed in claim 11, wherein the concentration of $NH_3$ is calculated by employing both the difference in the amount of radiation which passes through said fluid at two selected points within said wavelength range and a calibration curve.

15. The method of claim 1, wherein the concentration of NO in a fluid is measured and the selected wavelength range is from about 2100 Angstroms to about 2200 Angstroms.

16. The method as claimed in claim 13, wherein the concentration of NO is calculated by employing both the difference in the amount of radiation which passes through said fluid at two selected points within said wavelength range and a calibration curve.

17. The method of claim 1, wherein the concentration of $SO_2$ in a fluid is measured and the selected wavelength range is from about 2270 Angstroms to about 2300 Angstroms.

18. The method as claimed in claim 15, wherein the concentration of $SO_2$ is calculated by employing both the difference in the amount of radiation which passes through said fluid at two selected points within said wavelength range and a calibration curve.

19. A device for determining the concentration of at least one component in a fluid, comprising:
a radiation source;
a radiation detection means for measuring the amounts of radiation transmitted through said fluid at a plurality of wavelengths within a selected wavelength range;
a chamber disposed between said radiation source and said radiation detection means; and
calculation means for adjusting said measured amounts by compensating for wavelength dependent variations in said amounts due to factors other than absorption of radiation by said fluid and for determining the concentration of said component by performing a peak-to-trough measurement using said adjusted amounts.

20. The device of claim 19 wherein said fluid is a gas and said component is $NH_3$.

21. The device of claim 19 wherein said fluid is a gas and said component is NO.

22. The device of claim 19 wherein said fluid is a gas and said component is $SO_2$.

23. A method for determining radiation affecting characteristics of a fluid component, comprising the steps of:
(a) introducing said component into a chamber;
(b) passing radiation through said chamber;
(c) flowing into said chamber a diluting fluid;
(d) removing a mixture of the diluting fluid and the component from the chamber; and
(e) measuring the amount of radiation which passes through said chamber at a plurality of points within a wavelength range wherein said component absorbs radiation, and repeating the measurement at a plurality of times as said component is progressively diluted.

24. The method of claim 23, further comprising the step of:
calculating a concentration of said component by performing a peak-to-trough measurement on a selected peak within said range at each of said plurality of times.

25. The method of claim 23, further comprising the step of:
calculating a concentration of said component by determining a difference in the amount of radiation which passes through said component at two selected points within said range at each of said plurality of times.

26. The method of claim 24, wherein said step of calculating comprises using reference data obtained from measurements performed on known concentrations of said component to calculate the concentration of said component.

27. The method of claim 23, further comprising the step of:
(a) calculating a baseline based on said measured amounts of radiation; and
(b) calculating a concentration of said component at each of said plurality of times by determining an area between a spectrum defined by said measured amounts and said baseline, and between a first wavelength and a second wavelength, wherein said first wavelength is less than the wavelength of said peak and said second wavelength is greater than the wavelength of said peak.

28. The method of claim 23, further comprising the steps of:
storing values indicative of the amounts of radiation which pass through at least one of said points at said plurality of times; and
determining interim values indicative of the amounts of radiation which pass through said component at interim times.

29. The method of claim 28, wherein said step of determining comprises performing a regression analysis on said stored values.

30. A method for substantially negating a measured effect of an interfering component of a sample fluid, comprising the steps of:
(a) introducing said interfering component into a chamber;
(b) passing radiation through said chamber;
(c) flowing into said chamber a diluting fluid;
(d) measuring the amount of radiation which passes through said component at a plurality of points in a first wavelength range, wherein said interfering component and at least one other component of the sample fluid to be measured absorb radiation, and at a plurality of points in a second wavelength range, wherein substantially only said interfering component absorbs radiation, at a plurality of times as said component is progressively diluted;
(e) measuring the amount of radiation which passes through said sample fluid at a plurality of points in said first range and at a plurality of points in said second range;

(f) matching said measured amounts of radiation which pass through said sample fluid in said second range to amounts determined from said measured amounts of radiation which pass through said interfering component in said second range; and (g) determining, responsive to said step of matching, a difference between corresponding measured amounts of radiation which pass through said sample fluid in said first range and determined amounts of radiation which pass through said interfering component in said first range.

31. The method of claim 30, further comprising the step of determining, based on said measurements made in step (d), a relationship between the amount of radiation which passes through said interfering component and the concentration of said interfering component for each of said plurality of points in said first range and each of said plurality of points in said second range.

32. The method of claim 31, wherein said step of matching comprises determining, based on said relationships, a concentration of said interfering component corresponding to a measured amount of radiation passing through said sample fluid in said second range.

33. The method of claim 32, wherein said step of determining a difference comprises:

determining a difference between the measured amounts of radiation which pass through said sample fluid at a plurality of points in said first range and the amounts of radiation which pass through said interfering component at said plurality of points in said first range, wherein the amounts of radiation which pass through said interfering component are determined by using said relationships and said determined concentration.

34. The method of claim 30, wherein said step of matching comprises:

calculating a difference in the amount of radiation which passes through said sample fluid at two points within said second range;

determining a difference in the amount of radiation which passes through said interfering component at two points within said second range for a plurality of concentrations of said interfering component; and matching said calculated difference to an amount based on said determined differences.

35. The method of claim 30, wherein said interfering component comprises $SO_2$ and said second wavelength range is from about 2270 Angstroms to about 2300 Angstroms.

36. The method of claim 35, wherein said sample fluid comprises $NH_3$ and said first wavelength range is from about 2040 Angstroms to about 2120 Angstroms.

37. An apparatus for use in determining radiation affecting characteristics of a fluid component at a plurality of concentrations of the component; comprising a radiation source;

a chamber;

means for introducing a quantity of said component into said chamber;

means for flowing a diluting gas into said chamber; and radiation detection means capable of sensing the intensity of radiation within said selected wavelength range at a plurality of times as said component is progressively diluted by said diluting fluid.

38. The apparatus of claim 37 wherein said radiation detection means comprises a charge coupled device to sense the intensity of radiation at a plurality of wavelengths within said selected range.

39. The apparatus of claim 37, further comprising:

means to convert the output from the radiation detection means to a concentration of the fluid component based on a peak-to-trough measurement.

40. A method for measuring the concentration of a component in a fluid stream; comprising the steps of:

(a) measuring amounts of radiation which pass through a chamber containing a zero gas at a plurality of points within a wavelength range in which said component absorbs radiation;

(b) obtaining a stream sample by extracting fluid from said stream and flowing the extracted fluid into said chamber;

(c) measuring amounts of radiation which pass through said chamber containing said extracted fluid at a plurality of points within said range;

(d) obtaining a set of amounts by determining a difference between said amounts measured in step (c) and said amounts measured in step (a); and (e) determining the concentration of said component by performing a peak-to-trough measurement on said set of amounts and calculating the concentration of said component using reference data obtained from measurements performed on fluids of known concentration.

* * * * *